(12) United States Patent
Turner et al.

(10) Patent No.: US 9,415,234 B2
(45) Date of Patent: Aug. 16, 2016

(54) TISSUE HEATING PREDICTION USING FEEDPOINT EM FIELD DETERMINATION

(75) Inventors: Paul F. Turner, Bountiful, UT (US); Mark Hagmann, Salt Lake City, UT (US)

(73) Assignee: Pyrexar Medical Inc., Salt Lake City, UT (US)

( * ) Notice: Subject to any disclaimer, the term of this patent is extended or adjusted under 35 U.S.C. 154(b) by 918 days.

(21) Appl. No.: 13/543,611

(22) Filed: Jul. 6, 2012

(65) Prior Publication Data
US 2014/0012063 A1 Jan. 9, 2014

(51) Int. Cl.
*A61N 2/02* (2006.01)
*A61N 1/40* (2006.01)
*A61N 5/00* (2006.01)

(52) U.S. Cl.
CPC . *A61N 2/02* (2013.01); *A61N 1/403* (2013.01)

(58) Field of Classification Search
CPC ............. A61B 2018/183; A61B 18/1815
See application file for complete search history.

(56) References Cited

U.S. PATENT DOCUMENTS

| 2003/0055471 | A1* | 3/2003 | Fenn et al. ............ 607/101 |
| 2009/0157067 | A1* | 6/2009 | Kane et al. ............ 606/33 |
| 2011/0196365 | A1* | 8/2011 | Kim et al. ............ 606/33 |

OTHER PUBLICATIONS

Wust P, Hildebrandt B, Sreenivasa G, Rau B, Gellermann J, Riess H, Felix R, Schlag PM. Hyperthermia in combined treatment of cancer. *Lancet Oncology* 2002;3(8):487-97. Review Articles.

Falk MH and Issels RD. Hyperthermia in oncology. *Int J Hyperthermia* 2001;17(1):1-18.

Franckena M, Stalpers LJ, Koper PC, Wiggenraad RG, Hoogenraad WJ, van Dijk JD, Wárlám-Rodenhuis CC, Jobsen JJ, van Rhoon GC, van der Zee J. Long-term improvement in and treatment outcome after radiotherapy and hyperthermia in locoregionally advanced cervix cancer: an update of the Dutch Deep Hyperthermia trial. *Int J Radiat Oncol Biol Phys* 2008;70(4):1176-1182.

Franckena M, Lutgens LC, Koper PC, Kleynen CE, Van Steen-Banasik EM, Jobsen JJ, Leer JW, Creutzberg CL,. Dielwart MF, van Norden Y, Canters RAM, van Rhoon GC, van der Zee J. Radiotherapy and hyperthermia for treatment of primary locally advanced cervix cancer: results in 378 patients. *Int J Radiat Oncol Biol Phys* 2009;73(1):242-250.

(Continued)

*Primary Examiner* — Kaitlyn Smith
*Assistant Examiner* — Yasamin Ekrami
(74) *Attorney, Agent, or Firm* — Thorpe North & Western, LLP

(57) ABSTRACT

The accuracy of tissue heating in a body when using a phased array hyperthermia system can be improved by using, in conjunction with the hyperthermia system, a program for predicting heating patterns within the tissue based upon a selected E-field value at each of the antenna energy feedpoints. The hyperthermia system includes circuitry necessary to provide information for calculating the complete EM field at each of the antenna feedpoints during treatment, and such calculated actual feedpoint EM fields are feed to the program to be used in place of the otherwise program generated e-fields in predicting the heating pattern produced by the hyperthermia system during treatment. Further initial operating parameters of the hyperthermia system can be set to produce calculated actual EM fields at the antenna feedpoints which approximate the E-field values used by the program in pretreatment optimizing of the heating pattern.

6 Claims, 6 Drawing Sheets

(56) References Cited

OTHER PUBLICATIONS

Issels RD, Lindner LH, Verweij J, Wust P, Reichardt P, Schem B-C, Abdel-Rahman S, Daugaard S, Salat C, Wendtner CM, Vujaskovic Z, Wessalowski R, Jauch KW, Dürr HR, Ploner F, Baur-Malnyk A, Mansmann U, Hiddermann W, Blay JY, Hohenberger P. Neo-adjuvant chemotherapy alone or with regional hyperthermia for localized high-risk soft-tissue sarcoma: a randomized phase 3 multicentre study. *The Lancet Oncology*, 2010;11(6):561-570.

Canters, RA; Wust, P; Baker, JF; Van Rhoon, CG. A literature survey on indicators for characterizations and optimization of SAR distributions in deep hyperthermia, a plea for standardization. Int J Hyperthermia 2009; 25(7); 593-608.

Sreenivasa G, Gellermann J, Rau B, Nadobny J, Schlag P, Deuflhard P, Felix R, Wust P. Clinical use of the hyperthermia treatment planning system hyperplan to predict effectiveness and toxicity. *Int J Radiation Oncology Biol Phys* 2003;55(2):407-419.

Nadobny J, Fahling H, Hagmann MJ, Turner PF, Wlodarczyk W, Gellermann JM, Deuflhard P, Wust P. Experimental and numerical investigation of feed-point parameters in a 3-D hyperthermia applicator using different FDTD models of feed networks. *IEEE Trans Biomed Eng* 2002;49(11):1348-1359.

Seebass M, Beck R, Gellermann J, Nadobny J, Wust P. Electromagnetic phased arrays for regional hyperthermia: optimal frequency and antenna arrangement. *Int J Hyperthermia* 2001;17(4):321-336.

Wust P, Berger J, Fahling H, Nadobny J, Gellermann J, Tilly W, Rau B, Petermann K, Felix R. Scanning E-field sensor device for online measurements in annular phased-array systems. *Int J Radiation Oncology Biol Phys* 1999;43(4):927-937.

Wust P, Seebass M, Nadobny J, Deuflhard P, Monich G, Felix R, Simulation studies promote technological development of radiofrequency phased array hyperthermia. *Int J Hyperthermia* 1996;12(4):477-494.

Wust P, Nadobny J, Seebass M, Stalling D, Gellermann J, Hege H, Deuflhard P, Felix R. Influence of patient models and numerical methods on predicted power deposition patterns. *Int J Hyperthermia* 1999;15(6):519-540.

Wust P, Nadobny J, Seebass M, Dohlus JM, John W, Felix R. 3-D computation of E fields by the Volume-Surface Integral Equation (VSIE) method in comparison with the Finite-Integration Theory (FIT) method. *IEEE Trans Biomed Eng* 1993;40(8):745-759.

Gellermann J, Wust P, Stalling D, Seebass M, Nadobny J, Beck R, Hege H, Deuflhard P, Felix R. Clinical Evaluation and Verification of the Hyperthermia Treatment Planning System Hyperplan. *Int J Radiation Oncology Biol Phys* 2000;47(4):1145-56.

Franckena M, Canters R, Termorshuizen F, Van Der Zee J, Van Rhoon G. Clinical implementation of hyperthermia treatment planning guided steering: A cross over trial to assess its current contribution to treatment quality. *Int J Hyperthermia* 2010;26(2):145-157.

Wust, P; Gellermann, J; Beier, J; Wegner, S; Tilly, W; Troger, J; Stalling, D; Oswald, H; Hege, HC; Deuflhard, P; Felix, R.:, Evaluation of Segmentation Algorithms for Generation of Patient Models in Radiofrequency Hyperthermia. Phys Med Biol. 43:11, 3295-3307.

Wust, P; Fahling, H; Wlodarczyk, W; Seebass, M; Gellermann, J; Deuflhard, P; Nadobny, J:, Antenna Arrays in the SIGMA-eye Applicator: Interactions and Transforming Networks., 2001, Med Phys. 28:8, 1793-1805.

Wust, P; Beck, R; Berger, J; Fahling, H; Seebass, M; Wlodarczyk, W; Hoffmann, W; Nadobny, J:, Electric Field Distributions in a Phased-Array Applicator With 12 Channels: Measurements and Numerical Simulations., 2000, Med Phys. 27:11, 2565-2579.

Wust, P.; Seebass, M.; Nadobny, J.; Felix, R.:, Electromagnetic deep heating technology., 1995, Thermo-Radiotherapy and Thermo-Chemotherapy. 2:105-119.

Wust, P.; Meire, T.; Seebas, M.; Fahling, H.; Petermann, K.; Felix, R.:, Noninvasive prediction of SAR distributions with an electro-optical E field sensor., 1995, Int J Hyperthermia. 11:2, 295-310.

Wust, P.; Nadobny, J.; Seebass, M.; Dohlus, M.; Felix, R.:, Software constituents of a patient-specific hyperthermia 3D-planning system., 1991, Strahlentherapie und Onkologie. 167:6, 338.

Wust, P.; Nadobny, J.; Felix, R.; Deuflhard, P.; Louis, A.; John, W.:, Strategies for optimized application of annular-phased-array systems in clinical hyperthermia., 1991, nt J Hyperthermia. 7:1, 157-173.

Wust, P.; Nadobny, J.; Felix, R.; Deuflhard, P.; John, W.; Louis, A.:, Numerical approaches to treatment planning in deep RF-hyperthermia. Strahlentherapie und Onkologie. 165:10, 751-757.

Lee, WM; Ameziane, A; van den Biggelaar, AM; Rietveld, PJ; van Rhoon, GC:, Stability and Accuracy of Power and Phase Measurements of a VVM System Designed for Online Quality Control of the BSD-2000 (-3D) DHT System., Jan. 2003, Int J Hyperthermia. 19:1, 74-88.

Franckena, M; Canters, R; Termorshuizen, F; VanDerZee, J; Van Rhoon, G:, Clinical Implementation of Hyperthermia Treatment Planning Guided Steering: A Cross Over Trial to Assess Its Current Contribution to Treatment Quality., Mar. 2010, Int J Hyperthermia. 26:2, 145-157.

Van Der Wal, Edwin; Franckena, Martine; Wielheesen, Dennis H.M.; Van Der Zee, Jacoba; Van Rhoon, Gerard C.:, Steering in Locoregional Deep Hyperthermia: Evaluation of Common Practice With 3D-Planning., Dec. 2008, Int J Hyperthermia. 24:8, 682-693.

Das, S.K.; Clegg, S.T.; Ansher, M.S.; Samulski, T.V.:, Simulation of electromagnetically induced hyperthermia: A finite element gridding method, Dec. 1995, Int J Hyperthermia. 11:6, 797-808.

Clegg, S.T.; Das, S.K.; Fullar, E.; Anderson, S.; Blibin, J.; Oleson, J.R.; Samulski, T.V.:, Hyperthermia treatment planning and temperature distribution reconstruction: A case study., 1996.

Sullivan, D.:, Mathematical methods for treatment planning in deep regional hyperthermia., May 1991, IEEE Transactions on Microwave Theory and Techniques. 39:5, 864-872.

Bakker, J; Paulides, M; Westra, A; Schippers, H; Van Rhoon, G:, Design and Test of a 434 MHz Multi-channel Amplifier System for Targeted Hyperthermia Applicators., Int J Hyperthermia. 26:2, 158-170, 2012.

\* cited by examiner

TISSUE HEATING PREDICTION USING FEEDPOINT EM FIELD DETERMINATION

BACKGROUND OF THE INVENTION

1. Field

The present invention relates generally to systems and methods for irradiating targets with electromagnetic radiation, and more specifically to systems having arrays of dipole antennas and associated control system for controlling application of electromagnetic radiation to targets through phased array power steering.

2. State of the Art

The use of electromagnetic (EM) energy to heat tissue for the treatment of disease is well known. Electromagnetic energy applicators, such as microwave energy antennas, can be arranged with respect to the tissue to be treated to apply electromagnetic energy to the tissue to be treated to heat such tissue to desired treatment temperatures. Generally the tissue to be treated is diseased tissue, such as a tumor, located within normal healthy tissue which needs to be preserved and not treated. In such heat treatments, it is important to ensure that adequate heat is developed in the tissue to be treated without overheating surrounding healthy tissue. Various systems are currently available for applying electromagnetic energy to tissue to be treated to heat such tissue.

Some systems for applying electromagnetic energy to tissue to be treated located within normal tissue not to be treated control the position of the region of heating within the tissue through phased array power steering. In such systems, a plurality of electromagnetic applicators are arranged in an array around the tissue to be treated. Each applicator is separately powered by a separate channel of a multi-channel EM power system so different applicators are each provided with electronically controlled power of electronically controlled phase by respective separate power channels of the EM power system. This creates a desired phased array heating pattern steering capability. By controlling the relative power level and phase of the EM signal provided by each of the applicators to the tissue, the size, configuration, and location of the heating region can be controlled so as to provide adequate heat to the tissue to be treated while minimizing the heating of the normal healthy tissue not to be treated. The BSD-2000 system produced by BSD Medical Corporation, Salt Lake City, Utah, is a multi-channel phased array system that controls frequency, radiated power, and relative phase for each of a plurality of applicators. Each channel provides electronic control of power and phase and is connected to a different applicator. This allows electronic steering and shaping of the heating region.

In phased array heating systems, a plurality of applicators positioned around the tissue to be treated apply EM signals to the tissue from different directions so that the signals interact, such as by constructive interference, to create a heating zone in the tissue. In the use of phased array heating systems, the control of the relative power levels and phase of each applicator of the plurality of applicators is important in order to provide a desired heating region and heating pattern to adequately heat the tissue to be heated to provide the desired treatment while minimizing the heating of the normal healthy tissue surrounding the tissue being treated. There are many factors affecting the characteristics of the various EM signals in the tissue and the interactions between the signals. This makes it difficult to accurately control the positioning of and the heating pattern of the heating zone and to reduce the possibility of hot spots outside the heating zone.

Pretreatment planning using modeling has become an important aspect of providing heat treatment to body tissue. In general, pretreatment planning can be used to plan the treatment to be administered to a patient. While various degrees of pretreatment planning are used, the most comprehensive pretreatment planning usually involves the use of a computer program to simulate the heating patterns predicted by the program to be produced by particular applicators placed in particular locations or patterns in and/or around the tissue to be treated and operated at particular operating parameters such as particular frequencies, particular phases, particular power levels, etc. These simulation programs provide for the designation by a user of the location, size, and shape of the tissue mass to be treated and the position of the tissue mass in relation to the applicators. The user can then select particular operating parameters such as particular frequencies, particular phases, particular power levels, etc. for particular applicators and the simulation program produces a predicted heating distribution pattern. These simulated predicted heating distribution patterns are compared to the location, size, and shape of the tissue to be treated to determine how good the match is between the simulated heating pattern and the location, size, and shape of the actual tissue to be treated. The goal is to ensure that during the actual treatment adequate heat is developed in the diseased tissue to be treated without overheating surrounding healthy tissue. If a particular simulated predicted heating distribution pattern does not correspond well to the size and shape of the tissue to be treated, the user or the simulation program can make changes in the number of applicators used, their locations, the properties of the applicators, and/or the applicator operating parameters to try to obtain a better match.

The end result of the pretreatment planning simulation is a representation of a predicted heating distribution pattern that has been chosen as predicting the closest match to the desired treatment, i.e., the distribution pattern as predicted by the simulation program to provide the best treatment of the diseased tissue. As indicated above, a predicted simulated heating distribution pattern is produced taking into account specific positioning of the one or more applicators, specific applicator characteristics, and specific applicator operating parameters. Therefore, the predicted simulated heating distribution pattern chosen to produce the best tissue treatment indicates the applicator positioning, applicator characteristics, and applicator operating parameters predicted to provide the chosen heating distribution pattern. In setting up for the actual treatment, the treatment system is set up to operate at the same operating parameters used to obtain the chosen predicted simulated heating distribution pattern. With this set up and operation, it is predicted that the actual treatment result in the patient will be the treatment as shown by the chosen predicted simulated heating distribution pattern. Thus, the chosen simulated heating distribution pattern obtained in the pretreatment simulation provides the user with the optimized applicator positioning, applicator characteristics, and applicator operating parameters for the user to use during actual treatment of the patient.

However, the actual results obtained during treatment may be different from the predicted results so it is important to monitor the actual treatment to ensure that it proceeds as planned and expected. Various factors contribute to inaccuracies in the simulated treatment, such as the complexity of the treatment system and the accuracy of the model used to predict the treatment. In phased array heating systems, the plurality of applicators apply EM signals to the tissue from different directions so that the signals interact, such as by constructive interference, to create the heating zone in the tissue. There are many factors affecting the characteristics of the various EM signals in the tissue and the interactions between the signals. Further, because a phased array system has a plurality of antennas, there is cross coupling between various antennas that can affect the signals produced. This makes it difficult to accurately predict the positioning of the heating zone and the heating distribution in the heating zone and to predict locations of hot spots both inside and outside the heating zone.

The BSD-2000 phased array hyperthermia system uses an array of dipole antennas in a ring that surrounds the patient's body, with a water filled bolus interface between the system antennas and the patient's body. The antennas used are dipole couplets, i.e., two parallel side-by-side dipole antennas which are separated by and have their feedpoints connected by a coupling tee transmission line. In one model of the BSD-2000, four such dipole couplets (eight microwave dipole antennas) are arranged around the patient with each couplet attached to a separate channel of the BSD 2000 system. The currently used arrangement of four dipole couplets is a Sigma 60 applicator. In another model of the BSD-2000, twelve such dipole couplets (twenty four microwave dipole antennas) are arranged around the patient in three longitudinally spaced rings of four couplets each, with each couplet attached to a separate channel of the BSD 2000 system. The currently used arrangement of twelve dipole couplets is a Sigma Eye applicator. The use of numerical modeling to predict the specific absorption rate (SAR) of the EM power applied to the tissue and the resulting heating distribution in the tissue in patients treated using the BSD-2000 phased array hyperthermia system has been an ongoing research and development project since the 1980's. Such a numerical model could be used not only for pretreatment planning but also for interactive treatment control during treatment. Such development efforts begun at BSD Medical Corporation in the 1980's and continued at the University of Utah, Dartmouth, and Stanford University, have resulted in the creation by Nadobny and Seebass of Berlin of what is now known as the SigmaHyperPlan patient specific pretreatment planning program.

The SigmaHyperPlan is a numerical predictive program that uses a patient specific dielectric model generated from CT or MR scans of the tissue to be treated and the tissue around the tissue to be treated in the patient to calculate the SAR distribution within the patient for various frequency, relative power, and phase steering conditions for the array. The SigmaHyperPlan is used to predict the heating patterns that will be created within specific patients based on specific system operating parameters prior to treatment with the BSD-2000 and includes optimization of steering to maximize the predicted heating of target tumors. The BSD-2000 currently controls the forward power and phase and monitors the forward power and phase as well as reflected power for each of the channels driving RF power to each of the dipole antenna couplets of the Sigma applicators at various operating frequencies of the systems. With control of these variables and the monitoring of these variables for each of the antenna couplets, various assumptions have been made in the SigmaHyperPlan program in order to predict the SAR and the temperature distribution in the patient. The SigmaHyperPlan was developed based on the assumption that the feedpoint EM-fields, i.e., the EM field at the feedpoint of each dipole antenna, is directly based on the forward power and phase of the forward power driven to that couplet. In modeling each of the dipole antennas, it is further assumed that each of the dipole antennas in a dipole couplet have the same feedpoint E-field power and phase. Therefore, the SigmaHyperPlan program for modeling the Sigma Eye applicator can have an input of 12 forward powers and 12 forward power phases. The SigmaHyperPlan program for modeling the Sigma 60 applicator can have an input of four forward powers and four forward power phases. The numerical methods used in the SigmaHyperPlan are either finite difference time domain (FDTD) or finite element (FE) methods.

In pretreatment planning use of the SigmaHyperPlan program, the patient specific dielectric model generated from CT or MR scans of the tissue to be treated and the tissue around the tissue to be treated is used in conjunction with selected feedpoint e-fields for the respective antennas of the antenna phased array to be used for treatment. The initial selected feedpoint E-fields can be provided by a user of the pretreatment program or the program can start with a default setting of the respective antenna feedpoint E-fields. The program runs a simulation to determine the predicted heating pattern based on the selected antenna E-fields. If that program does not provide the desired heating pattern desired to treat the tissue to be treated, the program changes the values of the selected E-fields in an iterative process until it finds the best predicted heating pattern to provide the desired treatment. The program then provides the operator with the forward power and forward power phase settings to use for each channel to provide the feedpoint E-field for each antenna based on the presumption that each antenna feedpoint E-field is produced directly by the value of input power and input power phase applied to the antenna.

It has been found that improvement in the SAR and heating distribution predictions provided by the SigmaHyperPlan program can be obtained by improving the accuracy of the feedpoint E field information used in modeling the dipole antennas for each dipole antenna couplet. As indicated above, the two dipole antennas in each dipole couplet are separated by and have their feedpoints connected by a coupling tee transmission line. Also, a tuning stub is usually included in this coupling tee transmission line. Rather than assuming that the feedpoint E-field power and phase for each of the dipole antennas of a dipole couplet are the same and are directly based on the forward power and phase of the power driven to that couplet, it has been found that the coupling tee transmission line affects the values of the forward power and phase driven to the antenna feedpoints and that cross coupling between various antennas can result in the feedpoint E-Fields not being the same as had been predicted based on forward power and forward power phase. Adjustments for this can be included in the SigmaHyperPlan model as explained in Nadobny J, Fahling H, Hagmann M J, Turner P F, Wlodarczyk W, Gellermann J M, Deuflhard P, Wust P., Experimental and numerical investigation of feed-point parameters in a 3-D hyperthermia applicator using different FDTD models of feed networks. *IEEE Trans Biomed Eng* 2002; 49(11):1348-1359. However, the described adjustments for this are directed mostly to the effects of the coupling tee transmission line and are very limited in consideration of cross coupling between channels.

While the SigmaHyperPlan, and other similar programs for use with phased array hyperthermia systems provide guidance in planning and in operation of the phased array systems, such programs are still not very accurate in predicting the SAR and heating patterns during actual use of the system. Careful monitoring of tissue heating during actual treatment is still necessary to ensure proper heat treatment of the diseased tissue and limited heating of the normal tissue.

SUMMARY OF THE INVENTION

The use of computer programs, such as the SigmaHyperPlan program, for providing predicted SAR and heating distributions when using phased array heating systems has the potential to aid in more selective delivery of heating power to a target tumor while minimizing the hotspots in a particular patient. There are algorithms in the SigmaHyperPlan which calculate optimized relative power and phase steering settings to achieve this goal. Other optimization methods could also be implemented such as SAR optimization. In addition, the SigmaHyperPlan program or other similar programs could serve as an online prediction of the SAR and heating patterns in a patient during actual treatment if such predicted SAR and heating patterns can be predicted more accurately. Such a more accurate program could then guide the operator to change the steering parameters to both achieve better tumor heating and to reduce heating in predicted potential hotspots. The more accurately the SigmaHyperPlan or other similar prediction programs can predict the SAR selective power delivery, the less dependent a treatment will be on temperature distribution information. If there is optimized SAR to the tumor along with minimal hot spots the steering parameters will be optimized. The use of feedback temperatures then simply provide the guidance for total power levels to maintain the prescribed temperatures in the tumor target area. The integration of hyperthermia heating with magnetic resonance (MR) imaging has been shown to enable temperature MR measured patterns to be compared to SigmaHyperPlan predictions to aid in automated adjustments of the steering parameters to change the MR measured patterns to correspond more with a predicted optimized heating pattern. However, increased accuracy in the predicted SAR and heating patterns is needed for such use.

The current SigmaHyperPlan program is limited by basing its predictions on the feedpoint E-field assumed to be determined by only the variables of the forward power and forward power phase provided by each channel of the hyperthermia system. Therefore, the only variables to optimize relative power and phase steering with which the program can work are the feedpoint E-fields assumed to be set directly by the forward power settings and forward phase settings for each of the separate channels of the system. Thus, the SigmaHyperPlan program indicates to the operator of the phased array hyperthermia system how to initially set the forward power output and forward power phase of each channel output in order to provide the predicted SAR and heating pattern based on the programs calculation of the E-fields. However, as indicated, when the E-filed is determined in the program based on the assumption that it results directly from the settings of the forward power and the forward power phase for each channel, the optimization that can be done and the accuracy of the predictions made by the program are very limited.

One area that would appear to have potential to significantly increase the accuracy of the predicted SAR and heating patterns is to base the program calculations on a determination of the full electromagnetic (EM) fields at the dipole antenna feedpoints rather than merely on the E-fields at the dipole antenna feedpoints derived only from forward power and forward power phase measurements. Use of correct values of the complete EM-fields at the dipole feedpoints is required by the SigmaHyperPlan model to arrive at more accurate solutions for SAR and heating distributions. As indicated, in phased array systems using a plurality of antennas positioned around a patient being treated, cross coupling and reflected power can and does occur between antennas which affects the antenna feedpoint E-fields. Cross coupled power places an E-field at the feedpoint of an antenna, but the direction of that energy travel is not to the tissue of the patient but backwards to the amplifier of the hyperthermia system which results in a different SAR pattern in the patient than if the E-field was radiating toward the patient. This E-field direction away from the patient may reduce or increase the net E-field at the feedpoint of the antenna depending on what the relative phase is between the interacting electric fields. If the cross coupling between antenna channels is large enough and the forward power of a channel is set low enough, the net power on a channel would be dominated by the cross coupling power that would be reflected power rather than forward power. These situation are not accounted for when calculating the feedpoint E-field directly from the forward power and forward power phase settings and using the assumption that the feedpoint E-field is always in the forward direction, i.e., toward the patient.

There have been suggestions that feedpoint measurement of E-Field or of E-field and phase can be made at each feedpoint, but these measurements also assume that the RF power measured is passing from the antennas to the tissue. In addition, if individual E-field sensors are provided to measure the net E-field amplitude and phase at or near each feedpoint in a system with multiple antennas, it would add a further undesirable level of complexity to the system (24 separate E-field sensors to a system using a Sigma Eye applicator) that would present many challenges to making an accurate and reproducable measurement from each E-field sensor. For example, various errors can be introduced with the use of multiple individual E-field sensors that must be controlled if such measurements are to be used for the calculation of predicted SAR patterns. The placement of each sensor at the same location relative to the respective feedpoint is important for obtaining accurate phase measurements. The greater error for such placement is the amplitude which is rapidly changing with distance away from the dipole feedpoint. The dipole feedpoint is dominated by rather high quasi-static fields that decrease rapidly with distance from the actual feedpoint. This may cause a designer to intentionally move the detector further from the feedpoint, but will then introduce additional errors for the detected phase which would be a result of other cross coupling channels and a loss of radiation field direction. If the feedpoint E-field is measured in the bolus space, the values obtained are more strongly influenced by the cross coupling from other channels than if the measurement is made outside the bolus. This is because the field that exists in the bolus includes a greater portion of the net power from the other channels. The closer the E-field measurement is made to the actual feedpoint the better the correlation of the fields at the feedpoint. If the same sensors are not used for all measurements, there would be additional errors introduced by the detection differences of the different sensors.

According to the present invention, a program, such as the SigmaHyperPlan program, for predicting the SAR of tissue to be heat treated in a body by a phased array hyperthermia system would base its predictions on an antenna model using the complete EM field at the antenna feedpoints rather than just the E-field at the antenna feedpoints. Such a program would then take into account the cross coupling between antennas. There is a difference between the E-field and the complete EM field. The radiating field of a dipole antenna can be completely predicted by knowing the complete EM field at the feedpoint of the dipole. Knowing only the E-field fails to clarify whether or not the net field is a transmitted (forward) field or a reflected field.

Further, according to the invention, a phased array hyperthermia system for applying electromagnetic energy to tissue to be heat treated in a body, and which is adapted for use in conjunction with a program for predicting the SAR of the tissue to be heat treated and providing suggested settings of the EM field at the respective dipole feedpoints to produce the predicted SAR, includes detector circuitry for each individual channel of the system and associated with the signal amplifier of each channel of the system to detect the forward output power and forward output power phase of the output of the channel and the reflected power and reflected power phase of reflected power received by the channel. The detected forward output power and forward output power phase and reflected power and reflected power phase are used in conjunction with a known length of RF transmission line connecting the output of the channel to a dipole antenna to remotely calculate the complete EM field at the connection of the RF transmission line to the dipole antennas and the complete EM field at the dipole antenna feedpoint. This can be used in control of the hyperthermia system during actual treatment of the patient. For control purposes, the actual measured antenna feedpoint EM field information is fed to the prediction program and used as the feedpoint EM field in the program calculation of the predicted heating pattern. If the program is adapted to this use, the actual measurements of forward output power and forward output power phase and reflected power and reflected power phase for each system channel are fed to the prediction program which then calculates the feedpoint EM fields for the respective antenna feedpoints and uses these EM fields in calculating the predictions of the SAR and heating distribution based on these actual EM field at the antenna feedpoints. These predicted SAR and heating patterns, now based on the actual measured complete EM fields at the antenna feedpoints, can then be compared to the desired heating patterns required for the desired treatment for the patient and various control changes can be made to conform these predicted SAR and heating patterns provided by the program to the desired treatment. As indicated, the determination of the complete EM field is made remotely by measurements of the forward power and phase and the reflected power and phase at the RF amplifier output. This eliminates the need for individual E-field sensors for each antenna feedpoint. The complete EM field calculated includes the net amplitude, phase, and travel direction.

The use of more accurate measurement of the complete EM fields at the feedpoints enable adjustments to be made to the forward power and the forward power phase settings during operation of the phased array system so that the measured feedpoint fields can be adjusted to match the optimized predicted values that were determined from the SigmaHyperPlan program's numeral prediction for the specific patient treatment during pretreatment planning.

THE DRAWINGS

In the accompanying drawings, which show the best mode presently contemplated for carrying out the invention:

DETAILED DESCRIPTION OF THE ILLUSTRATED EMBODIMENTS

Figure 1:
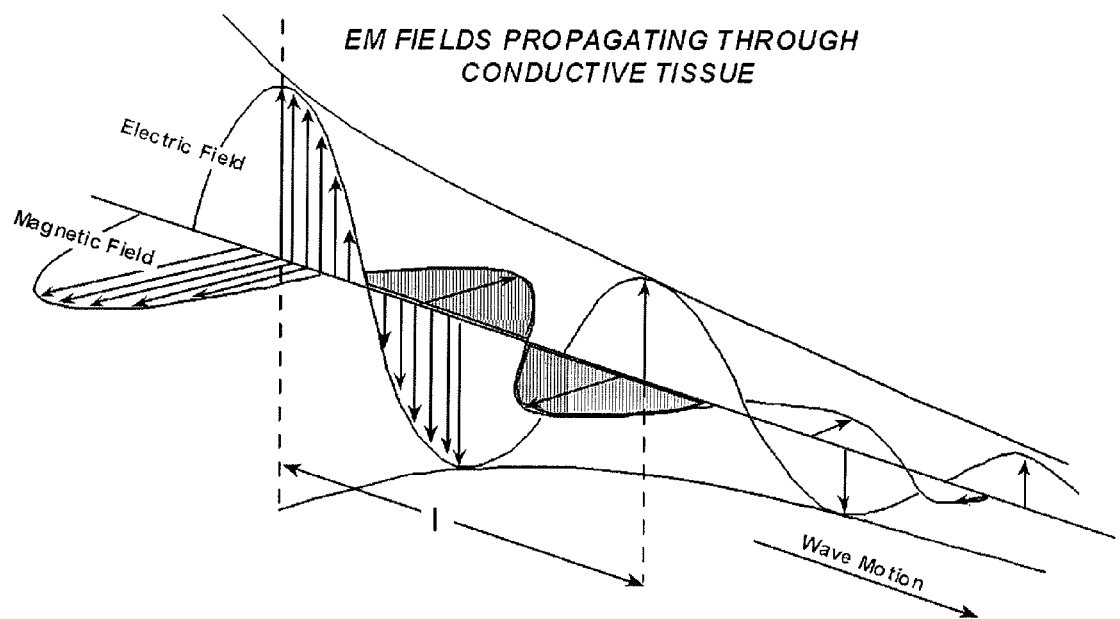
FIG. 1 is a schematic diagram of EM fields propagating through conductive tissue.

The present invention provides a phased array hyperthermia system providing a plurality of power output channels each having an output power amplifier for amplifying the channel power output signal. The output of an output power amplifier is connected by a coaxial cable to an applicator which transmits the power to the tissue to be treated. Such an applicator can take the form of a dipole antenna couplet having two parallel side-by-side dipole antennas which are separated by and have their feedpoints connected by a coupling tee transmission line. The coaxial cable is connected to the tee transmission line (couplet feedpoint) which directs the output of the power amplifier to the feedpoint of each of the dipole antennas. The output power amplifier measures the forward power provided by the amplifier, the phase of the forward power, the reflected power received back by the power amplifier, and the phase of the reflected power. By knowing the length of the coaxial cable, the four measurements indicated for each of the power amplifiers can be converted to the couplet feedpoint EM field amplitude, phase, and net flow direction using the phase delay and attenuation of the length of coaxial cable between the detectors and the couplet feedpoint. This allows the calculation of the complete EM field at the couplet feedpoint. This calculation of the complete EM field at the couplet feedpoint can be used to calculate the complete EM field at the individual dipole antenna feedpoints. The current BSD-2000 phased array hyperthermia system provides measurement of the forward power, forward power phase, and reverse power. It does not measure reverse power phase. Therefore, a phased array hyperthermia system of the invention can be made by adding the capability of measuring the reflected power phase to the current BSD-2000 phased array hyperthermia system. While this will produce a system capable of determining the complete EM field for each antenna feedpoint, it is also preferred to provide more accurate measurement of the forward power, forward power phase, reverse power, and reverse power phase.

The invention also provides a predictive program for use with the hyperthermia system for predicting the SAR and heating patterns produced in a particular patient when the phased array hyperthermia system is used in the treatment of the particular patient. The predictive program analyzes the interactions between the multiple signals applied to the tissue and interactions with the tissue to predict the SAR and resulting heating distribution. In order to analyze the interactions, the predictive program has to determine each of the multiple signals applied to the tissue so has to determine the radiated fields of each of the multiple antennas in the hyperthermia system. Since the radiated field of a dipole antenna can be completely predicted by knowing the complete EM field at the feedpoint of the antenna, the program, prior to actual treatment, bases its predictions of SAR and heating pattern using selected E-field values at the feedpoints of the respective dipole antennas of the system. Once actual treatment begins, the calculated actual complete EM fields can be used by the program to produce the more accurate predicted SAR and heating patterns determined to provide the desired treatment to the patient and to determine the optimized system settings needed to actually provide the determined complete EM fields at the respective dipole antennas.

As indicated, the radiated field of a dipole can be completely predicted by knowing the complete electromagnetic EM-field at the feedpoint of the dipole. Often this is confused by the thought that knowing the electric E-field is the same thing. Knowing only the E-field fails to clarify whether the net field is a transmitted or reflected field. For example the magnetic field pointing direction as shown in the FIG. 1 shows the pointing direction of the magnetic field coming from the source for a radiating field which propagates and is attenuated. If viewed from the originating side of this radiating field, the magnetic field is shown pointing to the observer's right side when the E-field is pointing up. However, if the same radiating field was viewed by a receiving antenna observer near the beginning of the radiation source, the magnetic field pointing direction would be pointing to the observer's left side even thought the pointing direction of the E-field was the same direction. This means that without knowing the net direction of the power flow at the antenna, the actual complete EM field at the feedpoint of an antenna is not adequately defined by only knowing the E-field magnitude and phase.

In phased array systems using a plurality of antennas positioned around a patient being treated, cross coupling and reflected power can and does occur between antennas which affects the antenna feedpoint E-field. Cross coupled power places an E-field at the feedpoint of an antenna, but the direction of that energy travel is not to the tissue of the patient but backwards to the amplifier of the hyperthermia system which results in a different SAR pattern in the patient than if the E-field was radiating toward the patient. This E-field direction away from the patient may reduce or increase the net E-field at the feedpoint of the antenna depending on what the relative phase is between the interacting electric fields. If the cross coupling between antenna channels is large enough and the forward power of a channel is set low enough, the net power on a channel would be dominated by the cross coupling power that would be reflected power rather than forward power. It has not been uncommon to see cross coupling values between the dipole antennas stacked end to end in the Sigma Eye applicator to be as high as −10 dB. This is from one dipole channel to another. These are synchronous fields and if three channels happened to be coupling −10 dB each and are of the same phase, the reflected power would be 95% as high as the forward power. Depending on such a cross coupling phase relative to the forward phase, the net power field at the feedpoint that would be measured by an E-field sensor could range from 0 to four times the actual forward power level even though the real net power radiated for a forward field would be near zero.

The assumption for the SigmaHyperPlan for the Sigma Eye applicator is that the forward power is much greater than the cross coupled net reflected power for each of the 12 dipole couplet channels. The entry of the relative power level assumes that the E-field is on a 50 ohm transmission line so that the power is determined by the square of the rms E-field divided by 50 ohms. The assumptions include that the tuning of the dipole couplet provides a low reflected power and low enough cross coupling so that the net power wave is assumed to be a forward wave. This may not be the case for higher reflected power and cross coupling between channels particularly when a channel forward power is reduced significantly.

This points out that a basic assumption of the prior art SigmaHyperPlan simulation program which uses an antenna model which assumes that the E-field at the antenna feedpoint is a forwardly transmitting field and not dominated by a reflecting field is not always correct. For most cases where the forward power that is applied to each dipole channel in a balanced amplitude, this would be the result and the model would be correct. However, if the cross coupling between antenna channels is large enough and the forward power of a channel is set low enough, it may be expected that there will be cases where the net power on a channel will be dominated by cross coupling power that will be more reflected than forward power. Therefore, for most cases in practical use the measure of only feedpoint E-fields will provide an accurate prediction of the SAR. However, there will be some cases where errors in the predicted SAR and heating patterns will occur when the program bases its predictions on the antenna feedpoint E-field rather than on the antenna feedpoint complete EM field.

A solution for this error is to measure the forward power and phase as well as the reflected power and phase. With these values the true net E-field magnitude, phase, and dominant energy flow direction can be determined for correct input to the SigmaHyperPlan program. Unfortunately the input to the SigmaHyperPlan program only includes entry of the relative net power which is assumed to all be radiating in the forward direction. So in cases where the feedpoint reflected power is greater than the forward power the closest power setting for the channel would be zero power even if there was actually a non-zero forward power.

The actual feedpoint E-field amplitude, phase, and direction of energy flow can be determined remotely at the amplifier by simply adding the measure of reflected power phase to what is measured in the BSD-2000 phased array hyperthermia system, i.e., forward power and phase and reflected power. If the cable lengths are know between the point of measurement and the point these fields are to be calculated for, it is a straight forward calculation to determine the feedpoint net E-field amplitude, phase and direction of radiation. Note the direction of radiation defines the pointing direction of the magnetic field.

The most accurate method to measure the actual full EM-Field for the feedpoint is to measure the forward power and forward power phase and the reflected power and the reflected power phase at some point along the transmission line between the amplifier and the dipole couplet with a known electrical distance between the measurement point and the feedpoint. With knowledge of the coaxial losses between the measurement point and the feedpoint, the net power E-field amplitude, phase, and flow direction can be determined for accurate modeling of the SAR patterns.

With these four measurements for each of the channel outputs of the RF multichannel amplifier these values can be converted to the couplet feedpoint EM-Field amplitude, phase, and net flow direction using the phase delay and attenuation of the length of coaxial cable between the detectors and the feedpoint. Such calculations can be included for each applicator used with the system.

The following provides the method and equations to determine the antenna net feedpoint electric field, power, and phase from the measurements of the amplifier channel output forward power, output forward power phase, reflected power, and reflected power phase.

Assumptions

It is assumed that the coaxial cable has a 50 ohm characteristic impedance between the amplifier output detectors and the dipole couplet feed point.

It is assumed that any tuner at the couplet feed point has approximately a 50 ohm impedance including any tuning that may be present to provide this impedance.

It is assumed the numerical model for calculating the SAR and tissue temperature distribution includes the antennas, the Tee coupling, and the tuning at the couplet feedpoint and uses the net electromagnetic field magnitude and net phase to create boundary conditions for the calculation.

The electromagnetic field at the feed point includes both an electric field and a magnetic field or dominant direction of travel of the energy. The directional net flow of power at the feed point is determined by the difference in phase of the electric and magnetic fields.

The phase values shown in the equations are assumed to be the conventional phase lead values. These can be converted to the equivalent phase lag values by changing value between positive and negative sign for the phase value.

The measurement of forward and reflected power and phase should be at approximately the same physical location at the output of the amplifier so that for total reflection when the cable is disconnected from the bi-directional coupler the phase of the forward and reflected power will be the same.

DEFINITIONS OF TERMS $\Phi nf$=Net Phase at antenna couplet feed point
$Enf$=Net electric field at antenna couplet feed point
$a$=cable attenuation in dB/meter
$Po$=Forward power output at amplifier channel
$\Phi po$=Forward phase at the amplifier output
$Pr$=Reflected power at the amplifier output
$\Phi ro$=Reflected phase at the amplifier channel output
$f$=frequency in Hertz
$L$=coaxial cable length in meters between detectors and antenna couplet feed point
$c$=speed of light in meters/second
$\in$=dielectric constant of coaxial cable
$\in o = 8.85 \times 10^{-12}$
Equations to Determine Feed Point Electric Field:

$$\lambda L = c/[f \cdot SQRT(\in \cdot \in o)]$$

$$\lambda Li = L/\lambda L - INT(L/\lambda L), \text{ the cable phase delay value between 0 and 359 degrees}$$

$$\Phi f\!f = \Phi f + \lambda Li \times 360 + \Phi po \text{ degrees, Forward wave phase at the feed point}$$

$$\Phi rf = -\lambda Li \times 360 + \Phi po + \Phi ro, \text{ Reflected wave phase at the feed point}$$

If Eff>Erf then the power wave net flow is outward from the dipole couplet, but not the net power wave flow is inward to the amplifier and in such a case the numerical model should account for the reverse flow of the dominant net power flow in its calculations.

The values of $\Phi f\!f$ and $\Phi rf$ are relative to the forward phase $\Phi po$ of the particular channel at the amplifier output.

$$E\!f\!f = SQRT[50Po \times 10^{(-L \cdot a/10)}], \text{ Forward } rms \text{ electric field magnitude at the feed point}$$

$$Erf = SQRT[50Po \times 10^{(L \cdot a/10)}], \text{ Reflected } rms \text{ electric field magnitude at the feed point}$$

The vector summation of the Eff and Erf and their respective phase provides the total net electric field magnitude (Enf) and phase ($\Phi nf$) at the couplet feedpoint.

$$Enf = Sqrt[(E\!f\!f \cos(\Phi f\!f) + Erf \cos(\Phi rf))^2 + (E\!f\!f \sin(\Phi f\!f) + Erf \sin(\Phi rf))^2]$$

$$\Phi nf = A\ TAN\ [(E\!f\!f \sin(\Phi f\!f) + Erf \sin(\Phi rf))/(E\!f\!f \cos(\Phi f\!f) + Erf \cos(\Phi rf))]$$

$$Pnf = 25 Enf^2, \text{ watts}$$

Therefore, the measurement of the values at the bi-directional coupler of Po, Pr, $\Phi po$, and $\Phi pr$ provide the input needed to determine the couplet feedpoint electric field's magnitude, net power, and relative phase for an array of antennas.

These measured parameters during an actual hyperthermia treatment with a phased array hyperthermia system can be input to the prediction program to predict the specific absorption rate (SAR) heating fields and estimated resulting temperature distributions in the various tissues of the human body being treated. The resulting SAR and temperature distributions calculated from these measurements can be compared to the intended heating patterns. Such a comparison could provide a means for an operator to determine if adjustments should be made on the output power and phase of the respective amplifier channels. If the resulting SAR and/or temperature patterns calculated from the actual net feedpoint values were adequately the same, there would be no need for further output parameter adjustments. If they were significantly different, the operator could initiate changes in the output power and phase settings for the amplifier system. The numerical models available have as a part of their processes various optimization algorithms which calculate the net power and phase at these couplet feedpoints for an optimized distribution of the SAR or temperatures in the tissues. The amplifier output power and phase for each of the power channels could then be changed to make the actual EM field power and phase at the couplet feedpoints match the calculated optimized values. This would then mean that the predicted optimized SAR and temperature distributions could be obtained in hyperthermia patients during treatment.

If during the treatment of a patient there was determined a need to alter the heating pattern to adapt to various clinical observations, the optimization for the SAR and temperature distribution could be altered with new constraints and a new optimization could be calculated. This could provide a changed set of amplifier parameters that could again be monitored and controlled using the monitored forward and reflected power and phase at the amplifier channels to determine the resulting SAR and temperature distributions in the patient.

Figure 2:
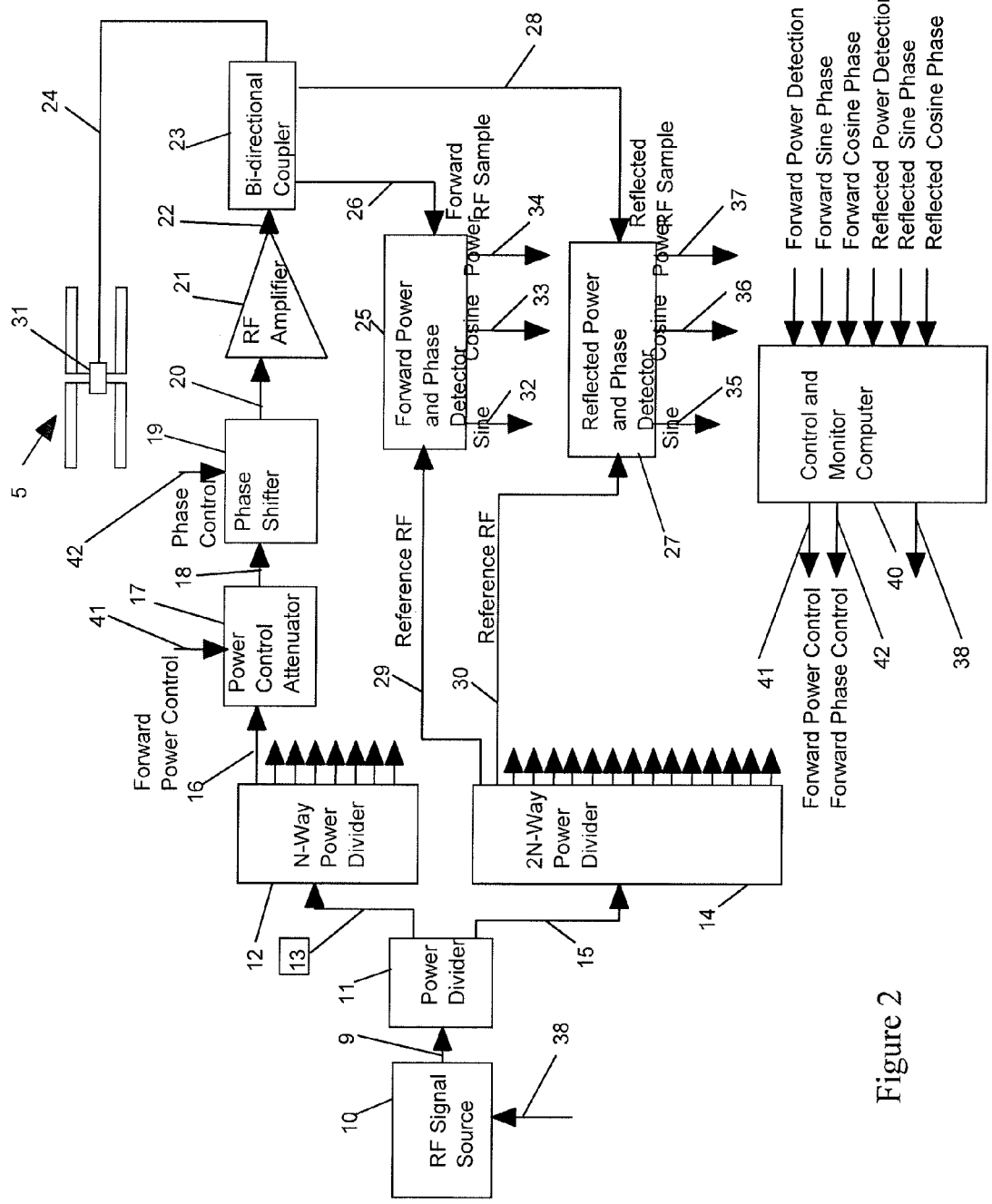
FIG. 2 is a block diagram of a basic phased array electromagnetic hyperthermia system of the invention.

FIG. 2 shows a block diagram for a basic phased array hyperthermia system of the invention. An RF signal source 10 provides an RF signal of the frequency to be transmitted to the patient. The RF signal is connected to a power splitter 11 with a transmission cable 9. The power splitter 11 divides the RF reference signal into two output paths 13 and 15. The transmission lines 13 are connected to a power splitter 12 with a number N of several outputs. The outputs of power splitter 12 are each connected to a channel represented by the path shown with transmission cable 16 that is connected to power control attenuator 17. The attenuator 17 allows adjustment of the RF power amplitude and directs its output to a phase shifter 19 through transmission line 18. The output of the phase shifter 19 is directed to a high power output amplifier 21 using transmission line 20. The output of output amplifier 21 is directed to a Bi-directional power coupler 23 with a transmission line 22. The Bi-directional power coupler provides an attenuated sample of the forward and reflected power wave flow along the coupler. The output of the coupler 23 is then connected to the antenna feed point 31 of an antenna couplet 5 through a coaxial transmission line 24 with a length L that is used in calculating the net electric field at the feed point 31. The feedpoint is used to direct the RF power to the individual antennas in antenna couplet 5. The antenna couplet 5 is typically a set of two parallel side-by-side dipole antennas that are separated by and have their feedpoints connected by a coupling tee transmission line.

The described connection of power control attenuator 17, phase shifter 18, RF output amplifier 21, and Bi-directional coupler 23 forms a separate channel of the system and is repeated for each output of the power divider 12 with the output of the Bi-directional coupler 23 of each channel being connected to a different antenna couplet 5 of the system.

The sampling output of the forward signal from bi-directional coupler 23 is directed by transmission line 26 to forward power and phase detector 25 and sampling output of the reflected power signal from bi-directional coupler 23 is directed by transmission line 28 to reflected power and phase detector 27. The forward power and phase detector circuit 25 compares the signal from line 26 with a reference signal from line 29 that is provided by a power divider 14 that has twice the number of RF outputs than the divider 12. The input signal for divider 14 is directed from the power divider 11 through the transmission cable 15. The reflected output signal from the Bi-directional coupler 23 is routed with transmission line 26 to reflected power and phase detector circuit 27 that is similar to the circuit of forward power and phase detector 25. This also receives a reference signal from the power divider 14 with a transmission line 30 to be compared to the signal from input line 28. A forward power and phase detector 25 and reflected power and phase detector 27 is provide for each channel of the system.

The operation of the power and phase detectors 25 and 27 each generate an output power amplitude measurement and a phase detection that is made up of a sine and cosine value. The forward power output is a dc voltage on wire 34, the Sine output is a dc voltage on wire 32, and the Cosine output is a dc voltage on wire 33. These three outputs are directed to a Control and Monitoring Computer 40 where the levels of these dc voltages represent different levels of the power and phase of the forward RF signal.

The reflected power output of detector 27 is a dc voltage on wire 37, the Sine output is a dc voltage on wire 35, and the Cosine output is a dc voltage on wire 36. These three outputs are also directed to the Control and Monitoring Computer 40 where the levels of these dc voltages represent different levels of the power and phase of the reflected wave.

The Control and Monitor Computer 40 receives the inputs from 32, 33, 34, 35, 36, and 37. The Control and Monitor Computer 40 provides output controls to the RF signal source 38 to control the frequency, to the power control attenuator 43 with line 41 to control the RF power level on the channel, and phase control to phase shifter 19 with control line 42.

The cable length of cable 24 and the lengths of lines 26 and 28 are used in the calculations to translate the detected phase and power from the detectors 25 and 27 to determine the net power, phase, and wave direction at antenna couplet feedpoint 31.

The circuit paths shown for lines 16, 29, and 30 along with those items that are shown to connect to these paths are duplicated for each of the N number of RF power channels in the phased array system.

Figure 3:
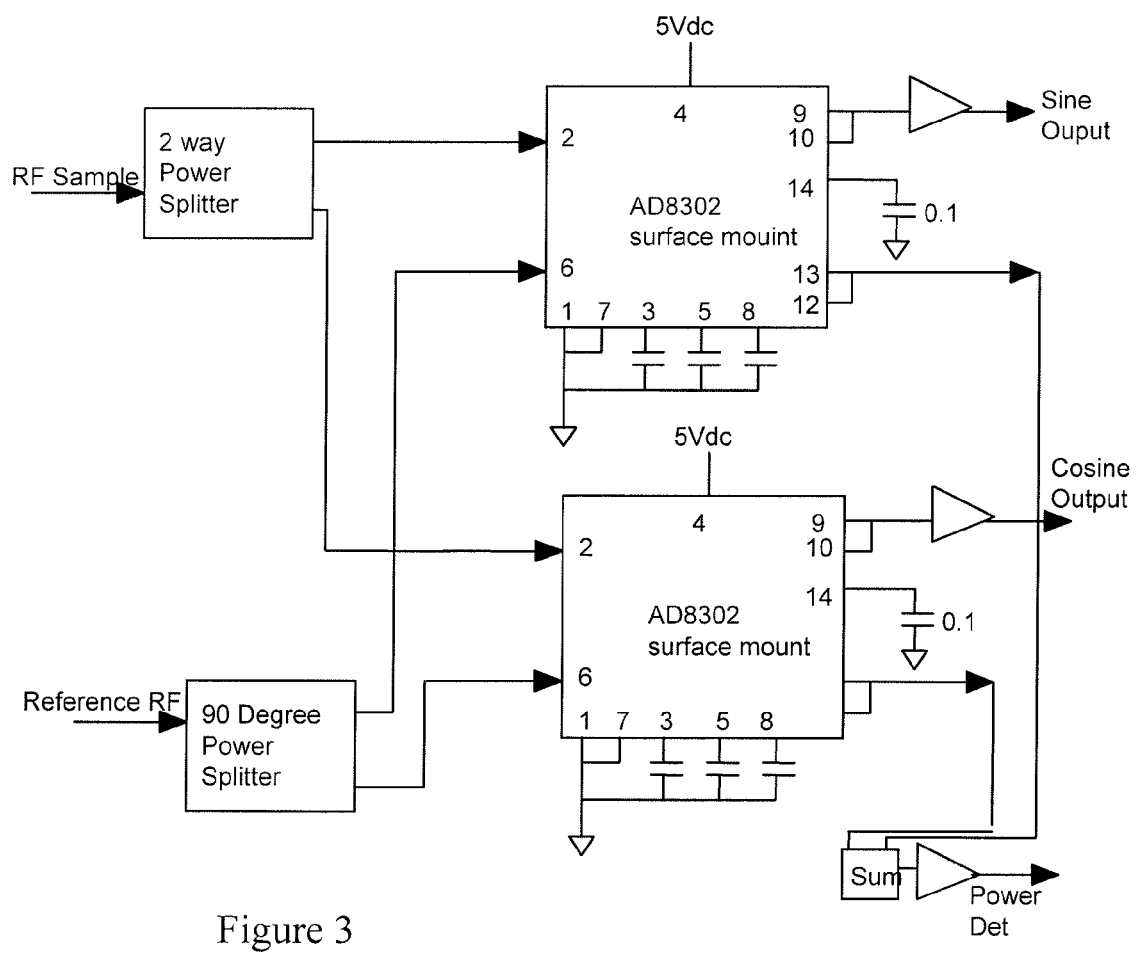
FIG. 3 is a schematic of each of the power and phase detector circuits usable with the invention.

FIG. 3 shows a schematic of the power and phase detector circuits used in each channel that are based on the Analog Device commercial integrated circuit chip AD8302. The inputs to this show the RF sample and reference RF described for FIG. 2. The outputs show the Sine, Cosine and Power level detected as a dc voltage as described for FIG. 2. The circuit of FIG. 3 uses a ninety degree power splitter to cause the two reference inputs to the two AD8302 chips to be ninety degrees out of phase with each other. This enables detection of a full 360 degrees. A single AD8302 only has a 180 degree output phase detection range.

Figure 4:
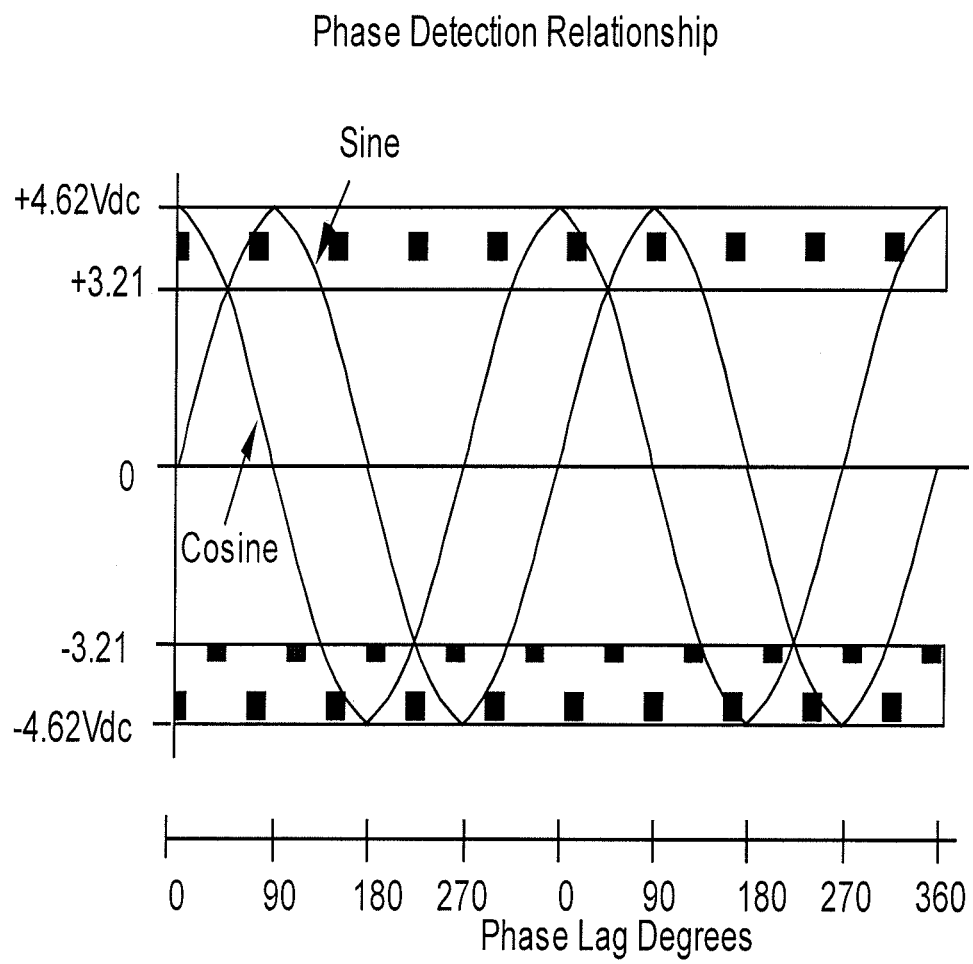
FIG. 4 is a diagram showing the relative phase of the sine and cosine output of the phase detector circuit.

FIG. 4 is a diagram showing how the relative phase of the sine and cosine output would differ in their output voltage. When the Sine is at maximum or minimum the Cosine is at a central point on the voltage swing. When the Cosine is maximum or minimum the Sine is at a central point. As shown in FIG. 4, the sine or cosine value that is between the −3.21 to +3.21 vdc levels would be used to measure the phase. Note the diagram does show that the voltage outputs from the AD8302 actually range between 0 and 1.8 vdc rather than that shown for −4.62 to +4.62 vdc.

Figure 5:
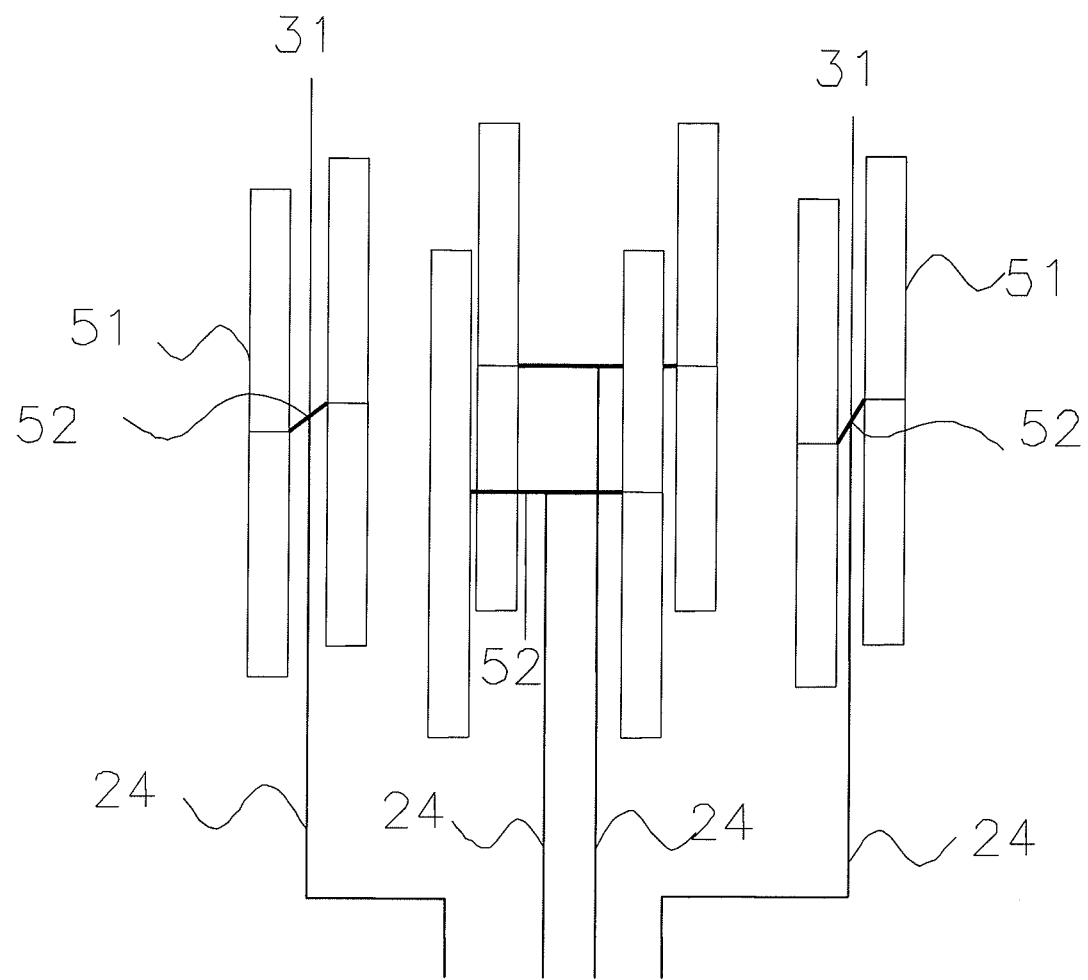
FIG. 5 is a diagram of an example dipole array that would be arranged in cylindrical form such as is used commercially in the BSD-2000 system.

FIG. 5 shows an example diagram of a dipole array that would be arranged in cylindrical form such as is used commercially in the BSD-2000 system. The dipole antennas 51 are connected to a transmission line tee 52 that is connected to the feedpoint circuit connecting the coaxial transmission lines 24 to the amplifier channels. These dipoles are oriented along a cylindrical outer form and are arranged in dipole couplets forming four two dipole groups in this diagram's example.

Figure 6:
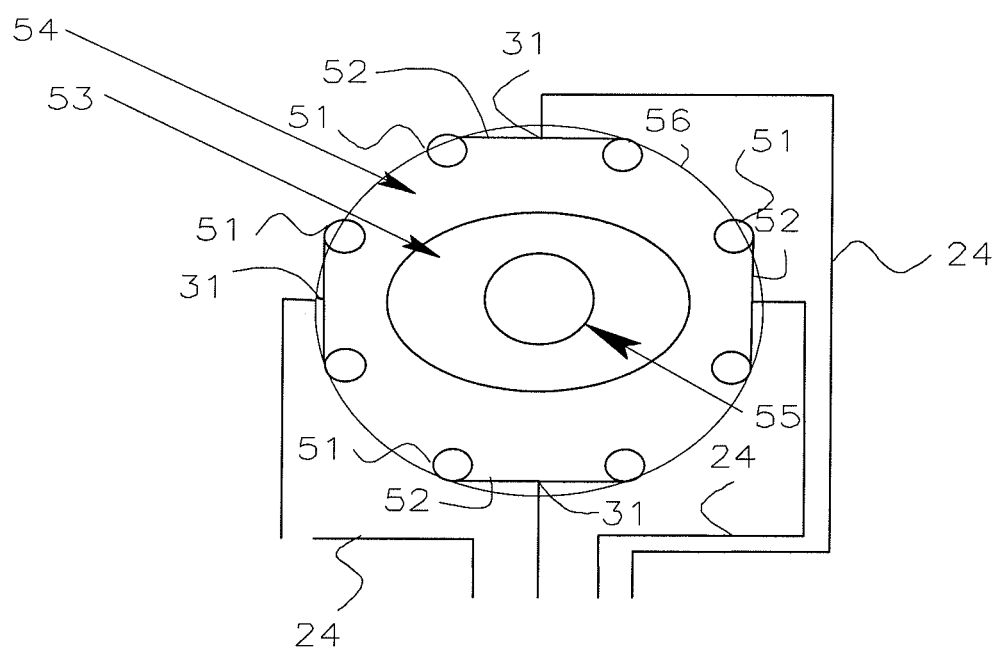
FIG. 6 is a an end view of the four channel array of the dipole antennas of FIG. 5 connected to lines which join with the dipole antenna feedpoints.

FIG. 6 shows an end view of the four channel array of the dipole antennas 51 connected to the tee lines 52 which join with the feedpoint connection point 31 using coaxial cables 24. The dipoles are arranged along a cylindrical shaped perimeter zone 56 and there is represented a patient body 53 that is surrounded by a bolus containing a dielectric fluid 54. Item 55 indicates the target region to be heated by the optimization process that utilizes the measurement of the feedback parameters described.

As evident from the above description, the invention includes a method of increasing the accuracy of tissue heating in a body when using a phased array hyperthermia system for heating tissue to be heat treated in the body in conjunction with a program for predicting at least one of the SAR and temperature distribution within the tissue of the body and predicting a heating pattern produced in the tissue by the hyperthermia system based upon selected E-field values at each of the antenna energy feedpoints, which includes the steps of determining the complete EM field at each antenna feedpoint during actual treatment of the patient and providing the determined actual complete EM field information to the program to be used in providing each antenna's selected E-field value used for predicting the heating pattern in the tissue. The program then provides the predicted SAR and/or predicted temperature distribution in the tissue using the calculated actual EM fields for each antenna feedpoint. The method then adjusts the operating controls of the phased array hyperthermia system to adjust the determined actual complete EM field at each of the antenna feedpoints to provide a desired patient treatment based upon the predicted heating pattern produced by the program in response to selected E-field values based upon the input to the program of the determined actual complete EM field at each antenna feedpoint. This method can be accomplished by using the Sigma-HyperScan program during actual treatment of a patient and feeding the information regarding the actual calculated complete EM fields at each antenna feedpoint into the program to be the basis for the feedpoint antenna E-fields used in the program to produce the predicted SAR and/or temperature distribution.

An alternate method of increasing the accuracy of tissue heating in a body when using a phased array hyperthermia system for heating tissue to be heat treated in the body in conjunction with a program for predicting at least one of the SAR and temperature distribution within the tissue of the body and producing a predicted heating pattern optimized to provide a desired heat treatment to the patient and providing suggested optimized operating parameters for producing the antenna feedpoint E-field values used to predict the optimized heating pattern based upon selected E-field values at each of the antenna energy feedpoints, includes the steps of determining the complete EM field at each antenna feedpoint during actual treatment of the patient, comparing the determined actual complete EM fields at each antenna feedpoint with the selected E-field values used by the program to predict the optimized heating pattern; and adjusting the operating parameters of the phased array hyperthermia system to produce actual E-fields at each of the antenna feedpoints approximating the selected E-field values used by the program to predict the optimized heating pattern. This method also can be accomplished by using the SigmaHyperScan program for pretreatment planning wherein the program provides an optimized predicted SAR or temperature distribution based on antenna feedpoint E-fields obtained using the SigmaHyperPlan E-field assumptions discussed above to provide an optimized heating pattern for providing the desired patient treatment. This then provides suggested optimized values for the antenna feedpoint E-fields. During actual treatment of a patient, the calculated actual complete EM fields at each antenna feedpoint are compared to the optimized E-fields used to predict the optimized heating pattern and the operating parameters of the phased array hyperthermia system (forward power and forward power phase) are adjusted to adjust the actual antenna feedpoint EM fields to approximate the program optimized antenna feedpoint E-fields. Once this is done, the actual EM field information can be feed into the SigmaHyperPlan program to produce the predicted SAR or temperature distribution based on the calculated actual EM field information to monitor the actual treatment.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow. For example, while the antennas have been described as dipole antennas arranged in couplets because these are currently used in the example BSD-2000 phased array hyperthermia system, other types of antennas and antenna arrangements can be used.

The invention claimed is:

1. A method of increasing the accuracy of tissue heating in a body when using a phased array hyperthermia system for heating tissue to be heat treated in the body, wherein the phased array hyperthermia system includes a plurality of antennas for applying electromagnetic energy to the tissue, wherein each antenna of the plurality of antennas has an antenna electromagnetic energy feed point, wherein the phased array hyperthermia system includes a plurality of separate channels, each channel of the plurality of separate channels having an output providing output power to at least one of the plurality of antenna by means of a transmission line of known length extending between the channel output and the antenna electromagnetic energy feedpoint of the at least one antenna of the plurality of antennas, and a detector for detecting a forward power, a forward power phase, a reflected power, and a reflected power phase at each channel output, comprising:

using a program for predicting at least one of a Specific Absorption Rate and a temperature distribution within the tissue of the body based upon selected E-field values at each of the antenna electromagnetic energy feedpoints, predicting a heating pattern produced in the tissue by the phased array hyperthermia system based upon a selected E-field value at each of the antenna electromagnetic energy feedpoints to provide a desired heat treatment to the tissue to be treated;

determining an actual complete EM field at each of the antenna electromagnetic energy feedpoints during treatment operation of the phased array hyperthermia system by calculating the actual complete EM field at the antenna electromagnetic energy feedpoint of a respective antenna of the plurality of antennas from the detected forward power, the detected forward power phase, the detected reflected power, and the detected reflected power phase at the channel output connected to the respective antenna electromagnetic energy feedpoint with the transmission line of known length;

providing the determined actual complete EM field at each of the antenna electromagnetic energy feedpoints to the program to be used in providing each antenna's selected E-field value used for predicting the heating pattern in the tissue; and adjusting operating controls of the phased array hyperthermia system to adjust the determined actual complete EM field at each of the antenna electromagnetic energy feedpoints to provide a desired patient treatment based upon the predicted heating pattern produced by the program in response to the selected E-field values based upon input to the program of the determined actual complete EM field at each antenna feedpoint.

2. A method of increasing the accuracy of tissue heating in a body when using a phased array hyperthermia system for heating tissue to be heat treated in the body, wherein the phased array hyperthermia system includes a plurality of antennas for applying electromagnetic energy to the tissue, and wherein each antenna of the plurality of antennas has an antenna electromagnetic energy feedpoint, wherein the phased array hyperthermia system includes a plurality of separate channels, each channel of the plurality of separate channels having an output providing output power to at least one of the plurality of antenna by means of a transmission line of known length extending between the channel output and the antenna electromagnetic energy feedpoint of the at least one antenna of the plurality of antennas, and a detector for detecting a forward power, a forward power phase, a reflected power, and a reflected power phase at each channel output, comprising:

using a program for predicting at least one of a Specific Absorption Rate and temperature distribution within the tissue of the body and predicting a heating pattern produced in the tissue by the phased array hyperthermia system based upon a selected E-field value at each of the antenna electromagnetic energy feedpoints, said program producing a predicted heating pattern optimized to provide a desired heat treatment to a patient and providing suggested optimized operating parameters for producing the selected antenna electromagnetic energy feedpoint E-field values used to predict the predicted heating pattern;

determining an actual complete EM field at each of the antenna electromagnetic energy feedpoints during treatment operation of the phased array hyperthermia system by calculating the actual complete EM field at the antenna electromagnetic energy feedpoint of a respective antenna of the plurality of antennas from the detected forward power, the detected forward power phase, the detected reflected power, and the detected reflected power phase at the channel output connected to the respective antenna electromagnetic energy feedpoint with the transmission line of known length;

comparing the determined actual complete EM fields at each antenna electromagnetic energy feedpoint with the selected E-field values used by the program to predict the heating pattern; and adjusting operating parameters of the phased array hyperthermia system to produce actual E-fields at each of the antenna electromagnetic energy feedpoints approximating the selected E-field values used by the program to predict the optimized heating pattern.

3. A phased array hyperthermia system for applying electromagnetic energy to tissue to be heat treated in a body and which increases the accuracy of applying the electromagnetic energy to the tissue to more accurately provide a desired patient treatment, said phased array hyperthermia system including a plurality of antennas for applying the electromagnetic energy to the body tissue with each antenna having an electromagnetic energy feedpoint, and said phased array hyperthermia system adapted for use in conjunction with a program for predicting at least one of the SAR and temperature of the tissue to be heat treated by the phased array hyperthermia system, said program predicting the at least one of the SAR and temperature based upon selected E-field values for each antenna feedpoint, and providing suggested settings of the EM field at the respective antenna feedpoints to produce the predicted at least one of the SAR and temperature, said phased array hyperthermia system comprising:

a plurality of antennas, each antenna having an electromagnetic energy feedpoint;

a plurality of individual channels each providing an RF electromagnetic power signal output of independently adjustable amplitude and phase;

a plurality of RF transmission lines each of known length and each connecting the output of an individual channel to at least one of the plurality of antennas; and detection circuitry for each individual channel to detect the forward output power and forward output power phase of the output of the channel and the reflected power and reflected power phase of reflected power received by the channel, said detected forward output power and forward output power phase and reflected power and reflected power phase being used in conjunction with the known length of the RF transmission line connecting the output of the channel to the at least one of the plurality of antennas to calculate the complete EM field at the connection of the RF transmission line to the at least one of the plurality of antennas and the complete EM field at the at least one dipole antenna feedpoint.

4. A phased array hyperthermia system according to claim 3, wherein the plurality of antennas are a plurality of dipole antennas arranged as a plurality of dipole antenna couplets each having two parallel side-by-side dipole antennas which are separated by and have their respective feedpoints connected by a coupling tee transmission line which is connected to the end of the RF transmission line, and wherein the complete EM field calculated for the connection of the RF transmission line to the coupling tee transmission line is adjusted to calculate the complete EM field at the feedpoint of each of the dipole antennas of the dipole couplet.

5. A phased array hyperthermia system according to claim 4, wherein the program for predicting at least one of the SAR or temperature of the tissue to be heat treated, provides suggested optimized E-field settings for the respective dipole feedpoints to optimize the at least one of the SAR and temperature for a desired patient treatment, and wherein one of the phased array hyperthermia system and program includes means for comparing the complete EM fields calculated from the detected forward output power and forward output power phase and reflected power and reflected power phase and transmission line length for each antenna feedpoint with the suggested optimized E-field settings whereby control parameters of the phased array hyperthermia system can be adjusted so that the calculated complete EM field for each antenna feedpoint approximates the suggested optimized E-field setting.

6. A phased array hyperthermia system according to claim 4, wherein the program for predicting at least one of the SAR or temperature of the tissue to be heat treated, provides a display of the predicted at least one of the SAR and temperature based on the complete EM fields calculated from the detected forward output power and forward output power phase and reflected power and reflected power phase and transmission line length for each antenna feedpoint.

* * * * *